(12) United States Patent
Humes (10) Patent No.: US 8,048,419 B2
(45) Date of Patent: Nov. 1, 2011

(54) EXTRACORPOREAL CELL-BASED THERAPEUTIC DEVICE AND DELIVERY SYSTEM

(75) Inventor: H. David Humes, Ann Arbor, MI (US)

(73) Assignee: Innovative BioTherapies, Inc., Ann Arbor, MI (US)

( * ) Notice: Subject to any disclaimer, the term of this patent is extended or adjusted under 35 U.S.C. 154(b) by 77 days.

(21) Appl. No.: 11/670,123

(22) Filed: Feb. 1, 2007

(65) Prior Publication Data

US 2007/0269489 A1 Nov. 22, 2007

Related U.S. Application Data

(60) Provisional application No. 60/764,357, filed on Feb. 2, 2006.

(51) Int. Cl.
*A61K 39/00* (2006.01)
*A01N 63/00* (2006.01)
*G01N 33/554* (2006.01)

(52) U.S. Cl. ............... 424/140.1; 424/93.1; 436/519

(58) Field of Classification Search ............ None
See application file for complete search history.

(56) References Cited

U.S. PATENT DOCUMENTS

| | | |
|---|---|---|
| 3,313,289 A | 4/1967 | Kapral |
| 3,943,936 A | 3/1976 | Rasor et al. |
| 3,952,747 A | 4/1976 | Kimmell, Jr. |
| 4,309,776 A | 1/1982 | Berguer |
| 4,332,893 A | 6/1982 | Rosenberg |
| 4,378,016 A | 3/1983 | Loeb |
| 4,393,133 A | 7/1983 | Knowles et al. |
| 4,402,694 A * | 9/1983 | Ash et al. ............ 604/891.1 |
| 4,479,796 A | 10/1984 | Kallok |
| 4,494,531 A | 1/1985 | Gianturco |
| 4,503,569 A | 3/1985 | Dotter |
| 4,511,353 A | 4/1985 | Theeuwes |
| 4,586,922 A | 5/1986 | Theeuwes |
| 4,643,712 A | 2/1987 | Kulik et al. |
| 4,648,865 A | 3/1987 | Aigner et al. |
| 4,655,771 A | 4/1987 | Wallsten et al. |
| 4,673,391 A | 6/1987 | Kondo et al. |
| 4,685,918 A | 8/1987 | Amidon et al. |
| 4,771,773 A | 9/1988 | Kropf et al. |
| 4,775,483 A | 10/1988 | Mookerjea et al. |
| 4,777,049 A | 10/1988 | Magruder et al. |
| 4,781,177 A | 11/1988 | Lebigot et al. |
| 4,793,348 A | 12/1988 | Palmaz |
| 4,793,825 A | 12/1988 | Benjamin et al. |
| 4,817,600 A | 4/1989 | Herms et al. |
| 4,820,626 A | 4/1989 | Williams et al. |
| 4,832,055 A | 5/1989 | Palestrant |
| 4,865,585 A | 9/1989 | Theeuwes |
| 4,871,352 A | 10/1989 | Tran |
| 4,877,864 A | 10/1989 | Wang et al. |
| 4,878,913 A | 11/1989 | Aebischer et al. |
| 4,892,538 A | 1/1990 | Aebischer et al. |
| 4,911,717 A | 3/1990 | Gaskill, III |
| 4,938,742 A | 7/1990 | Smits |
| 4,985,017 A | 1/1991 | Theeuwes |
| 4,994,069 A | 2/1991 | Ritchart et al. |
| 5,026,365 A | 6/1991 | Rossini et al. |
| 5,035,891 A | 7/1991 | Runkel et al. |
| 5,053,008 A | 10/1991 | Bajaj |
| 5,059,205 A | 10/1991 | El-Nounou et al. |
| 5,104,399 A | 4/1992 | Lazarus |
| 5,147,379 A | 9/1992 | Sabbaghian et al. |
| 5,152,743 A | 10/1992 | Gorsuch et al. |
| 5,152,777 A | 10/1992 | Goldberg et al. |
| 5,160,320 A | 11/1992 | Yum et al. |
| 5,164,186 A | 11/1992 | Tsuru et al. |
| 5,178,864 A | 1/1993 | Lees et al. |
| 5,182,111 A | 1/1993 | Aebischer et al. |

(Continued)

FOREIGN PATENT DOCUMENTS

DE 3447202 7/1986

(Continued)

OTHER PUBLICATIONS

Coring Incorporated (Cryogenic Preservation and Storage of Animal Cells; Life Sciences, printed 2009; pp. 1-5).*
International Search Report for Application No. PCT/US2007/061468, mailed Oct. 9, 2008 (2 pages).
Fissell, W. H. et al., "Bioartificial Kidney Alters Cytokine Response and Hemodynamics in Endotoxin-Challenged Uremic Animals", Blood Purif, 2002, vol. 20, pp. 55-60.

(Continued)

*Primary Examiner* — Vanessa L Ford
*Assistant Examiner* — Lakia Tongue
(74) *Attorney, Agent, or Firm* — Goodwin Procter LLP (57) ABSTRACT

Extracorporeal cell-based therapeutic devices and delivery systems are disclosed which provide a method for therapeutic delivery of biologically active molecules produced by living cells in response to a dynamic physiologic environment. Exemplary designs are disclosed. In a first exemplary embodiment the device includes long hollow fibers in which a layer of cells are grown within the intraluminal volume or within a double hollow-filled chamber. In another exemplary embodiment the device includes a wafer or a series of wafers forms a substrate onto which cells are grown. The wafer(s) are then inserted into a device. The devices are intended to be extracorporeal. Disclosed is a device for delivering a pre-selected molecule, for example, a hormone, into a mammal's systemic circulation. The device may also deliver a member of different cell products. The device comprises an anchoring element that can be anchored to an inner wall of an extracorporeal tube for blood. The device also comprises a capsule that is held in place within the extracorporeal tube for blood or fluid by an anchor. The device is adapted to secure viable cells which produce and secrete the pre-selected molecule into blood or fluid passing the capsule. The invention also provides a minimally invasive method for percutaneously introducing into a preselected blood vessel or body cavity the device of the invention.

12 Claims, 6 Drawing Sheets

U.S. PATENT DOCUMENTS

| | | | |
|---|---|---|---|
| 5,200,181 A | 4/1993 | Soltys et al. |
| 5,232,696 A | 8/1993 | Lees et al. |
| 5,260,068 A | 11/1993 | Chen |
| 5,282,861 A | 2/1994 | Kaplan |
| 5,304,120 A | 4/1994 | Crandell et al. |
| 5,314,471 A | 5/1994 | Brauker et al. |
| 5,350,398 A | 9/1994 | Pavcnik et al. |
| 5,360,790 A | 11/1994 | Humes |
| 5,368,555 A | 11/1994 | Sussman et al. |
| 5,368,588 A | 11/1994 | Bettinger |
| 5,370,691 A | 12/1994 | Samson |
| 5,383,887 A | 1/1995 | Nadal et al. |
| 5,383,892 A | 1/1995 | Cardon et al. |
| 5,383,928 A | 1/1995 | Scott et al. |
| 5,403,917 A | 4/1995 | Boos et al. |
| 5,411,550 A | 5/1995 | Herweck et al. |
| 5,415,630 A | 5/1995 | Gory et al. |
| 5,419,760 A | 5/1995 | Narciso, Jr. et al. |
| 5,429,634 A | 7/1995 | Narciso, Jr. |
| 5,429,938 A | 7/1995 | Humes |
| 5,443,508 A | 8/1995 | Giampapa |
| 5,478,807 A | 12/1995 | Cronin et al. |
| 5,487,739 A | 1/1996 | Aebischer et al. |
| 5,534,025 A | 7/1996 | Moussy et al. |
| 5,549,674 A | 8/1996 | Humes et al. |
| 5,591,230 A | 1/1997 | Horn et al. |
| 5,609,629 A | 3/1997 | Fearnot et al. |
| 5,649,906 A | 7/1997 | Gory et al. |
| 5,651,174 A | 7/1997 | Schwartz et al. |
| 5,679,775 A | 10/1997 | Boos et al. |
| 5,681,278 A | 10/1997 | Igo et al. |
| 5,686,289 A | 11/1997 | Humes et al. |
| 5,696,087 A | 12/1997 | Tang et al. |
| 5,702,717 A | 12/1997 | Cha et al. |
| 5,704,910 A | 1/1998 | Humes |
| 5,713,853 A | 2/1998 | Clark et al. |
| 5,720,764 A | 2/1998 | Naderlinger et al. |
| 5,722,992 A | 3/1998 | Goldmann et al. |
| 5,733,327 A | 3/1998 | Igaki et al. |
| 5,735,897 A | 4/1998 | Buirge |
| 5,756,291 A | 5/1998 | Griffin et al. |
| 5,773,327 A | 6/1998 | Yamazaki et al. |
| 5,788,468 A | 8/1998 | Dewa et al. |
| 5,788,673 A | 8/1998 | Young et al. |
| 5,797,887 A | 8/1998 | Rosen et al. |
| 5,797,898 A | 8/1998 | Santini, Jr. et al. |
| 5,800,421 A | 9/1998 | Lemelson |
| 5,810,767 A | 9/1998 | Klein |
| 5,834,449 A | 11/1998 | Thompson et al. |
| 5,843,781 A | 12/1998 | Ballermann et al. |
| 5,855,892 A | 1/1999 | Potter et al. |
| 5,873,904 A | 2/1999 | Ragheb et al. |
| 5,876,446 A | 3/1999 | Agrawal et al. |
| 5,891,154 A | 4/1999 | Loeffler |
| 5,895,407 A | 4/1999 | Jayaraman et al. |
| 5,899,935 A | 5/1999 | Ding |
| 5,902,336 A | 5/1999 | Mishkin |
| 5,911,704 A | 6/1999 | Humes |
| 5,964,745 A | 10/1999 | Lyles et al. |
| 5,981,252 A | 11/1999 | MacPhee et al. |
| 6,017,362 A | 1/2000 | Lau |
| 6,022,333 A | 2/2000 | Kensey |
| 6,027,516 A | 2/2000 | Kolobow et al. |
| 6,027,520 A | 2/2000 | Tsugita et al. |
| 6,030,336 A | 2/2000 | Franchi et al. |
| 6,030,414 A | 2/2000 | Taheri |
| 6,036,725 A | 3/2000 | Avellanet |
| 6,056,734 A | 5/2000 | Jacobsen et al. |
| 6,059,825 A | 5/2000 | Hobbs et al. |
| 6,060,270 A | 5/2000 | Humes |
| 6,071,035 A | 6/2000 | McKelvy |
| 6,080,178 A | 6/2000 | Meglin |
| 6,093,199 A | 7/2000 | Brown et al. |
| 6,099,495 A | 8/2000 | Kinghorn et al. |
| 6,099,864 A | 8/2000 | Morrison et al. |
| 6,106,454 A | 8/2000 | Berg et al. |
| 6,113,608 A | 9/2000 | Monroe et al. |
| 6,113,621 A | 9/2000 | Wiktor |
| 6,126,673 A | 10/2000 | Kim et al. |
| 6,129,757 A | 10/2000 | Weadock |
| 6,132,458 A | 10/2000 | Staehle et al. |
| 6,136,011 A | 10/2000 | Stambaugh |
| 6,150,164 A | 11/2000 | Humes |
| 6,283,951 B1 | 9/2001 | Flaherty et al. |
| 6,290,728 B1 | 9/2001 | Phelps et al. |
| 6,410,320 B1 | 6/2002 | Humes |
| 6,440,734 B1 | 8/2002 | Pykett et al. |
| 6,491,666 B1 | 12/2002 | Santini, Jr. et al. |
| 6,548,299 B1 | 4/2003 | Pykett et al. |
| 6,561,997 B1 | 5/2003 | Weitzel et al. |
| 6,572,605 B1 | 6/2003 | Humes |
| 6,585,756 B1 | 7/2003 | Strecker et al. |
| 6,645,489 B2 | 11/2003 | Pykett et al. |
| 6,653,131 B2 | 11/2003 | Humes |
| 6,716,208 B2 | 4/2004 | Humes |
| 6,913,588 B2 | 7/2005 | Weitzel et al. |
| 6,942,879 B2 | 9/2005 | Humes |
| 6,991,933 B1 | 1/2006 | Upton et al. |
| 7,192,769 B2 | 3/2007 | Pykett et al. |
| 7,332,330 B2 | 2/2008 | Humes et al. |
| 7,442,546 B2 | 10/2008 | Humes |
| 2001/0041363 A1 | 11/2001 | Humes |
| 2002/0090388 A1 | 7/2002 | Humes et al. |
| 2002/0090389 A1 | 7/2002 | Humes et al. |
| 2002/0119566 A1 | 8/2002 | Humes |
| 2004/0096430 A1 | 5/2004 | Bauer |
| 2005/0019370 A1 | 1/2005 | Humes |
| 2005/0238687 A1 | 10/2005 | Humes |
| 2006/0019362 A1* | 1/2006 | Yu et al. ........................ 435/182 |
| 2006/0084170 A1 | 4/2006 | Pykett et al. |
| 2006/0177478 A1 | 8/2006 | Humes et al. |
| 2006/0194310 A1 | 8/2006 | Upton et al. |
| 2006/0286078 A1 | 12/2006 | Humes |
| 2007/0065942 A1 | 3/2007 | Wandinger-Ness et al. |
| 2007/0269489 A1 | 11/2007 | Humes |
| 2009/0060890 A1 | 3/2009 | Humes et al. |
| 2009/0081296 A1 | 3/2009 | Humes et al. |
| 2009/0130756 A1 | 5/2009 | Klann et al. |
| 2010/0136687 A1 | 6/2010 | Westover et al. |

FOREIGN PATENT DOCUMENTS

| | | |
|---|---|---|
| DE | 3941873 | 6/1991 |
| EP | 0117940 | 9/1984 |
| EP | 0341039 | 11/1989 |
| EP | 0350043 | 1/1990 |
| EP | 0560279 | 9/1993 |
| EP | 0598635 | 5/1994 |
| EP | 0604022 | 6/1994 |
| JP | 1052476 | 2/1989 |
| JP | 3502534 | 6/1991 |
| WO | WO-89/04655 | 6/1989 |
| WO | WO-90/06997 | 6/1990 |
| WO | WO-92/15676 | 9/1992 |
| WO | WO-93/06878 | 4/1993 |
| WO | WO-9317696 A1 | 9/1993 |
| WO | WO-94/15583 | 7/1994 |
| WO | WO-95/00654 | 1/1995 |
| WO | WO-9511048 A2 | 4/1995 |
| WO | WO-96/14397 | 5/1996 |
| WO | WO-96/14399 | 5/1996 |
| WO | WO-96/39098 | 12/1996 |
| WO | WO-97/12680 | 4/1997 |
| WO | WO-99/15629 | 4/1999 |
| WO | WO-99/48545 | 9/1999 |
| WO | WO-99/55360 | 11/1999 |
| WO | WO-99/63971 | 12/1999 |
| WO | WO-00/27999 | 5/2000 |
| WO | WO-00/64510 | 11/2000 |
| WO | WO-01/21760 | 3/2001 |
| WO | WO-01/21766 | 3/2001 |
| WO | WO-02/055136 | 7/2002 |
| WO | WO-02/056796 | 7/2002 |
| WO | WO-03/022125 | 3/2003 |
| WO | WO-03020104 A2 | 3/2003 |
| WO | WO-03077840 A2 | 9/2003 |
| WO | WO-03/095603 | 11/2003 |
| WO | WO-03/100010 | 12/2003 |

| WO | WO-2006138537 A2 | 12/2006 |
| WO | WO-2007/092735 | 8/2007 |
| WO | WO-2008/045498 A1 | 4/2008 |
| WO | WO-2009029801 A2 | 3/2009 |
| WO | WO 2010/019643 A2 | 2/2010 |
| WO | WO-2010/071692 A2 | 6/2010 |

OTHER PUBLICATIONS

Fissell, W. H. et al., "Bioartificial Kidney Amellorates Gram-Negative Bacteria-Induced Septic Shock in Uremic Animals", J. Am. Soc. Nephrol., vol. 14, 2003, pp. 454-461.
Greenfield et al., "Venous Interruption", Ch. 68, pp. 929-939 in Hamimovic's Vascular Surgery Principles and Techniques, Third Edition, Appleton and Lange, Norwalk, CT/San Mateo, CA.
Humes, H. D. et al., "Cell therapy with a tissue-engineered kidney reduces the multiple-organ consequences of septic shock", Crit Care Med, 2003, vol. 31, No. 10, pp. 2421-2428.
Humes, H. D. et al., "Initial clinical results of the bioartificial kidney containing human cells in ICU patinets with acute renal failure", Kidney International, 2004, vol. 66, pp. 1578-1588.
Humes, H. D. et al., "Metabolic Replacement of Kidney Function in Uremic Animcals with a Bioartificial Kidney Containing Human Cells", American Journal of Kidney Diseases, May 2002, vol. 39, No. 5, pp. 1078-1087.
Humes, H. D. et al., "Replacement of renal function in uremic animals with a tissue-engineered kidney", Nature Biotechnology, May 1999, vol. 17, pp. 451-455.
Humes, H. D. et al., "Tissue engineering of a bioartifical renal tubule assist device: In vitro transport and metabolic characteristics", Kidney International, vol. 55 (1999) pp. 2502-2514.
Marty, C. et al., "Circulating interleukin-8 concentrations in patients with multiple organ failure of septic and nonseptic origin", Critical Care Medicine, 1994, vol. 22, No. 4, pp. 673-679.
Pinsky, M. R. et al., "Serum cytokine levels in human septic shock. Relation to multiple-system organ failure and mortality", Chest, 1993, vol. 103, pp. 565-575.
Radovich, J. M., "Composition of Polymer Membranes for Therapies of End-Stage Renal Disease", Dialysis Membranes: Structure and Predictions, Contrib. Nephrol., Basel Karger, 1995, vol. 113, pp. 11-24.
Williams, W. et al., "Renal Bioreplacement Therapy (RBT) Reduces Mortality in ICU Patients with Acute Renal Failure (ARF)", Nov. 17, 2006, Abstract (1 page).
Irori (1997), AN 1997-226007, XP002201866 & WO 97 12680 A, Database WPI Section Ch, week 199720, Derwent Publications Ltd., London, GB.
International Search Report for Application No. PCT/US2007/061468, mailed Oct. 9, 2008 (2 pages).
Tumlin et al. (2005) "Effect of the Renal Assist Device (RAD) on Mortality of Dialysis-Dependent Acute Renal Failure: A Randomized, Open-Labeled, Multicenter, Phase II Trial" J. Am. Soc. Nephrol. vol. 16 p. 46A, abstract.
Buffington et al.(Apr. 7, 2008, submission date) NIH Small Business Innovation Research Proposal Phase II submission, Abstract provided (3 pages).
Buffington et al.(Apr. 7, 2008, submission date) NIH Small Business Innovation Research Proposal Phase I submission, Abstract provided (3 pages).
Agrawal A.M., et al. (2004) "Water Distribution Studies within Microcystalline Cellulose and Chitosan Using Differential Scanning Calorimetry and Dynamic Vapor Sorption Analysis," J Pharm Sci 93(7): 1766-1779.
Barbucci, R., et al. (2002) "Dependence of Water Uptake and Morphology of Hyaluronan- and Alginate-Based Hydrogels on pH and Degree of Crosslinking," Macromol. Chem. Phys. 203: 1292-1300.
Brockbank K.G.M., et al. (2007) "Cryopreservation Guide" Thermo Scientific white paper.
Fahy, G.M.,et al. (2006) "Cryopreservation of Complex Systems: The Missing Link in Regenerative Medicine Supply Chain," Rejuvenation Research 9(2): 279-291.
Mazur P. (1970) "Cryobiology: The Freezing of Biological Systems" Science 168 (934): 939-49.

Mazur, P. (1984) "Freezing of Living Cells: Mechanisms and Implications" Am J. Physiol 247: C125-C142.
Canaple, Laurence, et al. (2001) "Maintenance of Primary Murine Hepatocyte Functions in Multicomponent Polymer Capsules—In Vitro Cryopreservation Studies," Journal of Hepatology 34:11-18.
Itie, Laura J., et al. (2005) "Cryopreservation of Cell-Containing Poly(ethylene) Glycol Hydrogel Microarrays," Biotechnol. Prog., 21:1004-1007.
Kofron, M.D., et al. (2003) "Cryopreservation of Tissue Engineered Constructs for Bone," J. Orthop Res., 21(6):1005-10. (Abstract).
Liu, B.L., et al. (2007) "Freezing Osteoblast Cells Attached to Hydroxyapatite Discs and Glass Coverslips: Mechanisms of Damage," Science in China Series E: Technological Sciences, 21:248-256.
Liu, B.L., et al. (2002) "Response of Murine Osteoblasts and Porous Hydroxyapatite Scaffolds to Two-Step, Slow Freezing and Vitrification Processes," Cell Preservation Technology 1(1):33-44. (Abstract).
Liu, B.L., et al. (2004) "Vitrification Solutions for the Cryopreservation of Tissue-Engineered Bone," Cell Preservation Technology, 2(2):133-143.
Malpique, Rita, et al. (2010) "Alginate Encapsulation as a Novel Strategy for the Cryopreservation of Neurosperes," Tissue Engineering, 00(00):1-13.
Pegg, D.E. (2002) "Cryopreservation of Vascular Endothelial Cells as Isolated Cells and as Monolayers," Cryobiology, 44(1):46-53. (Abstract).
Vrana, N.E., et al. (2009) "Cell Encapsulation Within PVA-Based Hydrogels Via Freeze-Thawing: A One-Step Scaffold Formation and Cell Storage Technique," Journal of Tissue Engineering and Regenerative Medicine, 3:567-572.
Kim, et al. (2005) "Nephrogenic Factors Promote Differentiation of Mouse Embryonic Stem Cells into Renal Epithelia," Journal of the American Society of Nephrology 16(12): 3527-3534.
International Search Report for PCT/US2009/047522 mailed on Jul. 14, 2010 (4 pages).
Tumlin, et al. (2008) "Efficacy and Safety of Renal Tubule Cell Therapy for Acute Renal Failure," Am. Soc. Nephrol. 19(5): 1034-40 (Abstract).
Wu, et al. (2004) "Glutathione Metabolism and its Implications for Health," J. Nutr. 134(3): 489-92 (Abstract).
International Search Report for PCT/US2009/053516 mailed on Apr. 12, 2010 (4 pages).
Chertow, et al. (1998) "Independent Association Between Acute Renal Failure and Mortality Following Cardiac Surgery," Am. J. Med., 104(4): 343-348.
Bates, et al. (2001) "Mortality and Costs of Acute Renal Failure Associated with Amphotericin B Therapy," Clin. Infect. Dis., 32(5): 686-693.
Humes (1995) "Acute Renal Failure: Prevailing Challenges and Prospects for the Future," Kidney Int. 48: S26-S32.
Schrier, et al. (2004) "Acute Renal Failure and Sepsis," N. Engl. J. Med., 351(2): 159-169.
Shlipak, et al. (2004) "The Clinical Challenge of Cardiorenal Syndrome," Circulation, 110(12): 1514-1517.
Gottlieb, et al. (2002) "The Prognostic Importance of Different Definitions of Worsening Renal Function in Congestive Heart Failure," J. Card. Fail., 8(3): 136-141.
Fonarow, et al. (2005) "Risk Stratification for In-Hospital Mortality in Acutely Decompensated Heart Failure: Classification and Regression Tree Analysis," JAMA 293(5): 572-580.
Iglehart (1993) "The American Health Care System. The End Stage Renal Disease Program," N. Engl. J. Med., 328(5): 366-371.
Excerpts from United States Renal Data System: Annual Data Report (1998) Am. J. Kidney Dis., 32: S69-S80.
Xue, et al. (2001) "Forecast of the Number of Patients with End-Stage Renal Disease in the United States to the Year 2010," J. Am. Soc. Nephrol., 12(12): 2753-8.
Cukor, et al. (2007) "Psychosocial Aspects of Chronic Disease: ESRD as a Paradigmatic Illness," J. Am. Soc. Nephrol., 18(12): 3042-3055.

Collins, et al. (2005) "Excerpts from the United States Renal Data System 2004 Annual Data Report: Atlas of End-Stage Renal Disease in the Untied States," *Am. J. Kidney Dis.*, 45(1 Suppl 1): A5-7.

Humes, et al. (2003) "Renal Cell Therapy is Associated with Dynamic and Individualized Responses in Patients with Acute Renal Failure," *Blood Purif.*, 21(1): 64-71.

Fahy, et al., (2004) "Improved Vitrification Solutions Based on the Predictability of Vitrification Solution Toxicity," *Cryobiology*, 48: 22-35.

Upton, et al. (2002) "Bioprocessing. Biomimetic 3-D Matrix High-Density Cultures. Tutorial: Cytomatrix Spinner System Supports Growth of Primary Cells, Cell Lines, and Tumor Cell Biopsies," *Genetic Engineering News*, 22(6) (4 pages).

Craig (1993) "Outpatient Parenteral Antibiotic Therapy. Management of Serious Infections. Part I: Medical, Socioeconomic, and Legal Issues. Selecting the Antibiotic," *Hosp. Pract.* (Off. Ed.) Suppl. (1):16-20 and abstract.

Crystal, R.G. (1992) "Gene Therapy Strategies for Pulmonary Disease," *Am. J. of Medicine* 92: 6A-44S-6A-52S.

Danos et al. (1988) "Safe and Efficient Generation of Recombinant Retroviruses with Amphotropic and Ecotropic Host Ranges," *Proc. Nat'l. Acad. Sci.* 85: 6460-64.

Deedwania et al. (1998) "Spontaneous Conversion and Maintenance of Sinus Rhythm by Amiodarone in Patients with Heart Failure and Atrial Fibrillation-Observations from the Veterans Affairs Congestive Heart Failure Survival Trail of Antiarrhythmic Therapy (CHF-STAT)," *Circulation* 98: 2574-79.

Dranoff et al. (1993) "Vaccination with Irradiated Tumor Cells Engineered to Secrete Murine Granulocyte-Macrophage Colony-Stimulating Factor Stimulates Potent, Specific, and Long-Lasting Antitumor Immunity," *Proc. Nat'l. Acad. Sci.* 90: 3539-43.

Durack (1993) "Outpatient Parenteral Antibiotic Therapy. Management of Serious Infections. Part II Amenable Infections and Models for Delivery. Endocarditis," *Hosp. Pract.* (Off. Ed.) Suppl. (2): 6-9.

Dwarki et al. (1995) "Gene Therapy for Hemophillia A: Production of Therapeutic Levels of Human Factor VIII in vivo in Mice," *Proc. Nat'l. Acad. Sci. USA* 92: 1023-27.

Edelman et al. (1995) "c-*myc* in Vasculoproliferative Disease," *Circulation Research* 76(2): 176-82.

Gage (1998) "Cell Therapy," *Nature* 392: 18-24.

Garver et al. (1987) "Clonal Gene Therapy: Transplanted Mouse Fibroblast Clones Express Human alpha.I-Antitrypsin Gene in Vivo," *Science* 237: 762-64.

Gibaldi, ed. (1991) "Nonoral Medication," in *Biopharmaceutics and Clinical Pharmacokinetics*, Lea & Febiger, 4th Edition, Philadelphia, pp. 80-123.

Ginsberg (1994) "Lipoprotein Metabolism and its Relationship to Atherosclerosis," *Medical Clinics of N. Am.* 78(1): 1-20.

Glaser, V. (1995) "Bioreactor and Fermenter Suppliers," *Genetic Engineering News*.

Goldberg et al. (1987) "The Regulated Expression of Erythropoietin by Two Human Hepatoma Cell Lines," *Proc. Nat'l. Acad. Sci. USA* 84: 7972-76.

Golomb et al. (1996) "Controlled Delivery of a Tyrphostin Inhibits Intimal Hyperplasia in a Rat Carotid Artery Injury Model," *Atherosclerosis* 125: 171-82.

Greenfield et al. (1973) "A New Intracaval Filter Permitting Continued Flow and Resolution of Emboli," *Surgery* 73: 599-606.

Greenfield et al. (1977) "Clinical Experience with the Kim-Ray Greenfield Vena Caval Filter," *Ann. Surg.* 185: 692-98.

Greenfield et al. (1981) "Greenfield Vena Caval Filter Experience," *Arch. Surg.* 116: 1451-56.

Greenfield L.J. (1991) "Venous Thromboembolic Disease," Chapter 37 in *Vascular Surgery, A Comprehensive Review*, Moore, Ed., pp. 669-679.

Hamamori et al. (1995) "Myoblast Transfer of Human Erythropoietin Gene in Mouse Model of Rental Failure," *J. Clin. Invest.* 95: 1808-13.

Harjai et al. (1997) "Home Inotropic Therapy in Advanced Heart Failure, Cost Analysis and Clinical outcomes," *Chest* 112(5): 1298-303.

Haskel et al. (1991) "Relative Efficacy of Antithrombin Compared with Antiplatelet Agents in Accelerating Coronary Thrombolysis and Preventing Early Reocclusion," *Circulation* 83:1048-56.

Heeschen et al. (1999) "Troponin Concentrations for Stratification of Patients with Acute Coronary Syndromes in Relation to Therapeutic Efficacy of Tirofiban," *Lancet* 354: 1757-62.

Heras et al. (1990) "Hirudin, Heparin, and Pacebo During Deep Arterial Injury in the Pig The in Vivo Role of Thrombin in Platelet-Mediated Thrombosis," *Circulation* 82: 1476-84.

Higenbottam et al. (1998) "Treatment of Pulmonary Hypertension with the Continuous Infusion of a Prostacyclin Analogue, Iloprost," *Heart* 79: 175-79.

Hjalmarson et al. (2000) "Effects of Controlled-Release Metoprolol on Total Mortality, Hospitalizations, and Well-being in Patients with Heart Failure," *J. Am. Med. Ass'n.* 283(10): 1295-302.

Hoeben et al. (1991) "Toward Gene Therapy in Haemophilia A: Retrovirus-Mediated Transfer of a Factor VII Gene into Murine Haematopoietic Progenitor Cells," 341-45.

Hsu (1991) "Principles of Heparin-Coating Techniques," *Perfusion* 6: 209-19.

"Instructions for Use Titanium Greenfield Vena Cava Filter with 12 French Introducer System" 1-48, by Meditech (date unknown), Boston Scientific Corporation.

Jelkmann, W. (1992) "Erythropoietin: Structure, Control of Production, and Function," *Physiological Reviews* 72: 449-89.

Kato et al. (1984) "Magnetic Microcapsules for Targeted Delivery of Anticancer Drugs," *Appl. Biochem. and Biotechnol.* 10: 199-211.

Kaukinen et al. (1985) "Clinical Study on ZK 36 374: A New Stable Prostacyclin Analog for Treatment of Peripheral Vascular Disease," *Prostacyclin-Clinical Trials* (Gryglewski et al. Eds.), Raven Press, New York, pp. 23-29.

Kravitz (1993) "Outpatient Parenteral Antibiotic Therapy. Management of Serious Infections. Part I: Medical, Socioeconomic, and Legal Issues. Advances in I.V. Delivery." *Hosp. Pract.* (Off. Ed.) Suppl. (1): 21-27.

Kroon, et al. (1999) "The Rebound of Lipoproteins after LDL-Apheresis. Effects on Chemical Composition and LDL-Oxidizability." *Atherosclerosis* 147: 105-13.

Kurachi et al. (1993) "Gene Therapy of Hemophilia B" *Thromb. Haemost.* 70: 193-97.

Labeque et al. (1993) "Enzymatic Modification of Plasma Low Density Lipoproteins in Rabbits: A Potential Treatment for Hypercholesterolemia," *Proc. Nat'l. Acad. Sci.* 90: 3476-80.

Labhasetwar et al. (1994) "Sotalol Controlled-Release Systems for Arrhythmias: in Vitro Characterization, in Vivo Drug Disposition, and Electrophysiologic Effects," *J. Pharm. Sci.* 83(2): 156-64.

Labhasetwar et al. (1994) "Epicardial Administration of Ibutilide from Polyurethane Matrices: Effects on Defibrillation Threshold and Electrophysiologic Parameters," *J. Cardiovasc. Pharmacol* 24(5): 826-40.

Labhasetwar et al. (1998) "Prevention of Acute Inducible Atrial Flutter in Dogs by Using an Ibutilide-Polymer-Coated Pacing Electrode," *J. Cardiovasc. Pharmacol.* 31(3): 449-55.

Labhasetwar et al. (1998) "A DNA Controlled-Release Coating for Gene Transfer: Transfection in Skeletal and Cardiac Muscle," *J. Pharm. Sci.* 87(11): 1347-50.

Lacy et al. (1976) "Long-term Perifusion of Isolated Rat Islets in Vitro," *Diabetes* 25: 484-93.

Langer (1998) "Drug Delivery and Targeting," *Nature* 392: 5-10.

Lehmann et al. (1995) "Haemodynamic Evaluation of Two Regimens of Molsidomine in Patients with Chronic Congestive Heart Failure," *Eur. J. Clin. Pharmacol* 48: 109-14.

Li et al. (1987) "Influence of Drug Properties and Routes of Drug Administration on the Design of Sustained and Controlled Release Systems," *Controlled Drug Delivery* (Robinson et al. Eds.), 2nd Ed., Marcel Dekker, Inc., New York, Chapter 1, pp. 36-38.

Liguori et al. (1999) "Loop Diuretics Enhance the Secretion of Prostacyclin In Vitro, in Healthy Persons, and In Patients with Chronic Heart Failure," *Eur. J. Clin. Pharmacol.* 55: 117-24.

Lozier et al. (1994) "Gene Therapy and the Hemophilias," *J. Am. Med. Ass'n.* 271(1): 47-51.

Malchesky et al. (1993) "Are Selective Macromolecule Removal Plasmapheresis Systems Useful for Autoimmune Diseases or Hyperlipidemia?," *ASAIO J.* 39: 868-72.

Mandell, Douglas and Bennett's Principles of and Practice of Infectious Diseases (1979) Fourth Edition, Chapter 12 *Principles of Anti-Infective Therapy* p. 209.

Masuyama et al. (1990) "Effects of Nitroprusside on Transmitral Flow Velocity Patterns in Extreme Heart Failure: A Combined Hemodynamic and Doppler Echocardiographic Study of Varying Loading Conditions," *J. Am. Coll. Cardiol.* 16: 1175-85.

Maxwell et al. (1993) "Identification of the Renal Erythropoietin-producing Cells Using Transgenic Mice," *Kidney Int'l.* 44: 1149-62.

Meyer et al. (1994) "Local Delivery of r-Hirudin by a Double-Balloon Perfusion Catheter Prevents Mural Thrombosis and Minimizes Platelet Deposition After Angioplasty," *Circulation* 90: 2474-80.

Muller et al. (1996) "Sustained-Release Local Hirulog Therapy Decreases Early Thrombosis But Not Neointimal Thickening After Arterial Stenting," *Am. Heart J.* 131(2): 211-18.

Nashitz et al. (1993) "Thromboembolism in Cancer," *Cancer* 71: 1384-90.

Odell et al. (1991) "Beta2-Microglobulin Kinetics in End-Stage Renal Failure," *Kidney Int'l.* 39: 909-19.

Oliva et al. (1999) "Intermittent 6-Month Low-Dose Dobutamine Infusion in Severe Heart Failure: DICE Multicenter Trial," *Am. Heart J.* 138(2): 247-53.

Orloff et al. (1995) "Prevention of Venous Thrombosis in Microvascular Surgery by Transmural Release of Heparin from a Polyanhydride Polymer," *Surgery* 117(5): 554-59.

Racz et al. (1986) "Stability Study of Prostacyclin in Solution" *Pharmazie* 41 (H.11): 769-71.

Revillard et al. (1998) "Structure and Metabolism of Beta-2-Microglobulin," *Contr. Nephrol.* 62: 44-53.

Rogers et al. (1993) "Inhibition of Experimental Neointimal Hyperplasia and Thrombosis Depends on the Type of Vascular Injury and the Site of Drug Administration," *Circulation* 88(3): 1215-21.

Roman et al. (1992) "Circulating Human or Canine Factor IX from Retrovirally Transduced Primary Myoblasts and Established Myoblast Cell Lines Grafted into Murine Skeletal Muscle," *Somatic Cell and Molecular Genetics* 18: 247-58.

Sanaka et al. (1989) "Extracorporeal Hybridization of Proximal Renal Tubular Cells and an Artificial Membrane for the Purpose of Beta$_2$ Microglobulin Removal," *ASAIO Transactions* 35: 527-30.

Shapiro et al. (1997) "Primary Pulmonary Hypertension: Improved Long-Term Effects and Survival with Continuous Intravenous Epoprostenol Infusion," *J. Am. Coll. Cardiol.* 30: 343-49.

Shefer et al. (1993) "Extracorporeal Enzymatic Removal of Low Density Lipoproteins in Rabbits: Efficacy and Safety," *Int'l. J. Artif. Organs* 16 (4): 218-28.

Siden et al. (1992) "Epicardial Propranolol Administration for Ventricular Arrhythmias in Dogs: Matrix Formulation and Characterization," *Biomaterials* 13(11): 764-70.

Sindone et al. (1997) "Continuous Home Ambulatory Intravenous Inotropic Drug Therapy in Severe Heart Failure: Safety and Cost Efficacy," *Am. Heart J.* 134(5): 889-900.

Skuballa et al. (1987) "Chemistry of Stable Prostacyclin Analogues: Synthesis of Iloprost," *Prostacyclin and Its Stable Analogue Iloprost* (Gryglewski et al. Eds.), Springer-Verlag, Berlin Heidelberg, Germany, pp. 17-24.

Thompson et al. (1995) "Familial Hyoercholesterolaemia Regression Study: A Randomised Trial of Low-Density-Lipoprotein Apheresis," *Lancet* 345: 811-16.

Tice (date unknown) "Osteomyelitis," University of Washington, pp. 36-39.

Tice (1993) "Introduction," Proceedings of a Symposium held on Jan. 26 and 27, 1993, Sonoma, California, p. 5.

Tripathy et al. (1994) "Stable Delivery of Physiologic Levels of Recombinant Erythropoietin to the Systemic Circulation by Intramuscular Injection of Replication-defective Adenovirus," *Proc. Nat'l. Acad. Sci. USA* 91: 11557-61.

Tong et al. (1992) "Non-thrombogenic Hemofiltration System for Acute Renal Failure Treatment," *ASAIO J.* 38: M702-06.

Waller (1999) "Optimal Nitrate Therapy with a Once-Daily Sustained-Release Formulation of Isosorbide Mononitrate," *J. Cardiovasc. Pharmacol.* suppl. 2: S21-27.

Wollheim et al. (1990) "Isolation of Pancreatic Islets and Primary Culture of the Intact Microorgans or of Dispersed Islet Cells," *Methods in Enzymology* 192: 188-223.

Wollheim et al. (1990) "Establishment and Culture of Insulin-Secreting β Cell Lines," *Methods in Enzymology* 192: 223-35.

Yamamura et al. (1995) "Sustained Release of Basic Fibroblast Growth Factor from the Synthetic Vascular Prosthesis Using Hydroxypropylchitosan Acetate," *J. Biomed. Mater. Res.* 29(2): 203-06.

Yao et al. (1992) "Expression of human factor IX in mice after injection of genetically modified myoblasts," *Proc. Nat'l. Acad. Sci. USA* vol. 89: 3357-61.

Yao et al. (1993) "Implanted Myoblasts Not Only Fuse With Myofibers But Also Survive As Muscle Precursor Cells," *J. of Cell Sci.* 105: 957-63.

Yao et al. (1994) "Primary Myoblast-mediated Gene Transfer: Persistent Expression of Human Factor IX in Mice," *Gene Therapy* 1: 99-107.

Yu of al. (1998) "The Biologic Effects of Growth Factor-Toxin Conjugates in Models of Vascular Injury Depend on Dose, Mode of Delivery, and Animal Species," *J. Pharm. Sci.* 87(11): 1300-04.

Humes et al. (Feb. 16, 2007, submission date) "Nanofabricated Bioartificial Kidney," U.S. Army Med. Research and Materiel Command, Grant No. W81XWH-05-2-010, P00004, FY05 Modification, Abstract provided.

Humes et al. (Mar. 16, 2007, submission date) "Nanofabricated Bioartificial Kidney," U.S. Army Med. Research and Materiel Command, Grant No. W81XWH-05-2-0010, P00005, FY06 Modification, Abstract provided.

Humes et al. (Oct. 30, 2007, submission date) "Nanofabricated Bioartificial Kidney," U.S. Army Med. Research and Materiel Command, Grant No. W81XWH-05-2-0010, FY07 Modification, Abstract provided.

Buffington (May 2, 2006, project start date) "Cell Therapy for Septic Shock," National Institute of Diabetes and Digestive and Kidney Diseases, Grant No. 1R43DK074289-01, Abstract provided.

Buffington (May 2, 2006, project start date) "Cell Therapy for Septic Shock," National Institute of Diabetes and Digestive and Kidney Diseases, Grant No. 5R43DK074289-02, Abstract provided.

Buffington (May 2, 2006, project start date) "Cell Therapy for Septic Shock," National Institute of Diabetes and Digestive and Kidney Diseases, Grant No. 2R44DK074289-03, Abstract provided.

ALZA Corporation, DUROS implant technology, http://www.alza.com, printed Jan. 7, 2002 and Mar. 18, 2005.

ALZA Corporation, DUROS technology: how does it work? http://www.alza.com, printed Jan. 7, 2002 and Jan. 13, 2005.

ALZET Osmotic Pumps—A General Description, http: www.alzet.com, printed Jan. 7, 2002 and Jan. 13, 2005.

Acchiardo et al. (1989) "β2-Microglobulin Levels in Patients With Renal Insufficiency," *Am. J. of Kidney Diseases* 13(1): 70-74.

Aebisher et al. (1991) "Transplantation of Microencapsulated Bovine Chromaffin Cells Reduces Lesion-induced Rotational Asymmetry in Rats," *Brain Research* 560: 43-49.

Albert et al. (1992) "Evaluation of Various Gene Transfection Methods Into Human Myoblast Clones," *Transplantation Proceedings* 24: 2784-86.

Arosio et al. (1993) "Effects of Sustained-Release Isradipine on Blood Pressure and Peripheral Hemodynamics in Hypertensive Patients," *Clin. Ther.* 15(4): 705-13.

Badesch et al. (2000) "Continuous Intravenous Epoprostenol for Pulmonary Hypertension Due to the Scleroderma Spectrum of Disease," *Annals of Internal Medicine* 132(6): 425-34.

Berner et al. (1992) "Fundamental Concepts in Controlled Release" in *Treatise on Controlled Drug Delivery* (Kydonieus Ed), Marcel Dekker, Inc., New York, pp. 1, 14-15.

Buerk et al. (1982) "Arterial Wall Oxygen Consumption Rate Varies Spatially " *Am. J. Physiol.* 243(6): H948-58.

Cesario et al. (1998) "Beneficial Effects of Intermittent Home Administration of the Inotrope/Vasodilator Milrinone in Patients with End-Stage Congestive Heart A Preliminary Study," *Am. Heart J.* 135(1): 121-29.

\* cited by examiner

Variation on Extracorporeal Cell-Bearing Therapeutic Device and Delivery System

Device Design

NOSE CONE
porous nosecone, pore size excludes large molecules, passes ultra-filtrate/plasma equivalent CELL-BEARING UNIT:
Cells grown to tissue density within hollow walls of fibers.

FIG. 5

Method of Action

EXTRACORPOREAL CELL-BASED THERAPEUTIC DEVICE AND DELIVERY SYSTEM

CROSS-REFERENCE SECTION

This application claims the benefit of currently pending U.S. Provisional Application No. 60/764,357, filed Feb. 2, 2006.

FIELD OF THE INVENTION

The present invention relates to an extracorporeal therapeutic device for delivering therapeutic molecules into a body. More particularly, this invention relates to an extracorporeal therapeutic device containing viable cells. One way that the molecules can be delivered into a body is through blood circulation or other bodily fluids. When the device is introduced into the blood stream outside the body, the cells produce and secrete the therapeutic molecule into blood or fluid circulating past the device.

BACKGROUND OF THE INVENTION

Drug delivery devices useful for introducing therapeutic molecules into a mammal have been the subject of considerable research. In one aspect, the research has focused on the development of devices that deliver molecules produced from cellular metabolism. Efforts have also focused on producing an implantable cell based delivery system that can remain in a patient for an extended period of time.

An implantable device for delivering a pre-selected molecule, for example, a hormone, into a mammal's systemic circulation is described in U.S. Pat. No. 6,716,208, the entire contents of which is incorporated by reference. The device described comprises an implantable blood permeable element that can be anchored to an inner wall of an intact blood vessel and a capsule that is held in place within the blood vessel by the anchored blood permeable element. The capsule encloses viable cells which produce and secrete the preselected molecule into blood passing the capsule. The patent also describes a method for percutaneously introducing the device into a preselected blood vessel.

Intracorporeal cell based delivery devices must be sized to fit within a body, typically a body lumen (such as a blood vessel) and, accordingly, have certain size limitations because of the reduced-size requirements. Further, when an intracorporeal cell based delivery system is designed, the anchors used to attach the device to the body, e.g., blood vessel, must be configured to secure the device without introducing trauma to the body. Finally, implantable devices can be difficult to retrieve, especially if they are left within the body for an extended period of time.

In vitro experiments with a larger extracorporeal device utilizing porcine or human proximal tubule progenitor cells have shown differentiated transport and metabolic functions of the renal tubule assist device (RAD).[references 4-6] The bioartificial kidney (BAK) set-up consists of a filtration unit (a conventional synthetic hemofiltration cartridge) followed in series by the tubule (RAD) unit. The tubule unit is able to maintain viability because oxygen along with metabolic substrates and growth substances are delivered to the tubule cells from both intraluminal ultrafiltrate and blood in the extracapillary space. Immunoprotection of the cells is achieved due to the impenetrability of immunoglobulins and immunocompetent cells across the hollow fibers. Rejection of non-autologous cells does not occur.

Pre-clinical studies in large animals have demonstrated that the BAK successfully replaced filtration, transport, metabolic, and endocrinologic functions of the kidney in acutely uremic dogs.[5] Further pre-clinical experiments in acutely uremic dogs have also evaluated the influence of the RAD under stress states. Acutely nephrectomized animals were challenged with infusions of endotoxin (lipopolysaccharide) intravenously or with intraperitoneal administration of doses of viable E. Coli before treatment with either cell or sham control RADs in a BAK.[references 7,8] In these experiments, cell RADs provided metabolic renal replacement and resulted in higher anti-inflammatory plasma levels, better hemodynamic stability, and, in the E. Coli sepsis model, longer survival times compared to sham controls. To further evaluate the role of the BAK in septic shock, a swine model with normal kidney function was given large doses of E. Coli intraperitoneally.[reference 9] All animals developed acute tubular necrosis with oligo/anuria within 2-4 hours following administration, and RAD treatment resulted in better cardiovascular performance, lower plasma levels of the pro-inflammatory cytokines, and longer survival times compared to sham controls.

These supportive pre-clinical experiments were the basis for testing human cell RADs in Phase I/II and Phase II clinical trials in intensive care unit (ICU) patients with ARF and MOF. A favorable Phase I/II safety trial [reference 10] led to an FDA-approved, randomized, controlled, open-label Phase II investigation at 12 clinical sites to determine whether this cell therapy approach alters patient mortality. This Phase II study involved 58 patients, of whom 40 were randomized to RAD therapy and 18 made up a control group with comparable demographics and severity of illness. The early results have been as compelling as the Phase I/II results. Renal cell therapy improved the 28-day mortality rate from 61% in the conventional hemofiltration-treated control group to 34% in the RAD-treated group.[references 11,12] This survival impact continued through the 90- and 180-day follow-up periods (p<0.04), with the Cox proportional hazard ratio indicating that the risk of death was 50% of that observed in the conventional continuous renal replacement therapy group. This survival advantage with renal cell therapy was observed for various etiologies of ARF and regardless of organ failure number (1 to 5+) or the presence of sepsis. Subset analysis of patients with concomitant severe sepsis or septic shock demonstrated an incidence of sepsis of 73% and 67% in the cell therapy and conventional therapy groups, respectively. RAD therapy was associated with a mortality rate of 34% in patients with sepsis, compared to 67% in the conventional treatment group. Thus, these clinical results suggest a major effect on survival rates in these desperately ill patients. The clinical use of renal tubule cell therapy for patients with severe sepsis will not require this complex two-cartridge system with two extracorporeal pump systems, since most are not in ARF.

The present invention provides an extracorporeal cell based delivery system that is designed to address aspects of an intracorporeal cell based delivery system. Further, the present invention provides an extracorporeal device designed to introduce therapeutic agents into a mammal that secretes a pre-selected molecule or a combination of cell products directly into the blood stream or into a body fluid or body cavity and addresses the challenges of the prior art. The invention will be more clearly understood from the description, which follows.

Further, a miniaturized cell therapy device will not require extensive extracorporeal blood pump systems. In addition, a miniaturized device that could be stored at the clinical site for immediate use is required to succeed as a commercial product. The current RAD is stored at a central manufacturing facility at 37° C. and must be shipped at 37° C. to the clinical site, delaying treatment and adding to the cost of therapy. Development of a cell device that can be cryopreserved and stored at clinical sites can help safetly bring the device to market.

SUMMARY OF THE INVENTION

The present invention provides an extracorporeal therapeutic device for delivery of a pre-selected molecule or cell products into a mammal, for example, into the circulatory system or body fluids of a mammal. An embodiment of the invention enables molecules to be introduced into the circulatory system or a body cavity without invasive surgical procedures. Once the device is deployed it delivers the molecule directly into the blood stream or body fluid. In addition, the device of the invention is adapted to produce and thereafter secrete the pre-selected molecule or cell product into the blood stream or body fluid over a determined period of time. The extracorporeal device and method provide an easy and reproducible system for delivering therapeutically effective amounts of a gene product, for example, a hormone, growth factor, anti-coagulant, immunomodulator, or the like, directly into the blood stream or body fluid of the recipient without the disadvantages of an invasive implantation procedure.

An extracorporeal device that administers a preselected molecule(s) into the mammal over a predetermined period presents advantages over the prior art. An extracorporeal device has the advantage of being easily taken out of the circulation system compared to the efforts required to remove an implanted device. Accordingly, the present invention provides an extracorporeal device for delivering, over a determined period of time, a preselected molecule or cell products into the systemic circulation of a mammal. In another aspect, the present invention provides a method for non-surgically introducing the device into blood circulation of a mammal that is capable of delivering the preselected molecule or cell products into systemic circulation.

In one embodiment, the device includes a capsule that contains viable cells which produce and secrete the preselected molecule into the blood stream. The device may include an anchoring element, which anchors the device to an inner surface of a tube that circulates blood extracorporeally.

The term "extracorporeal circuit" as used in this specification embraces any tube or conduit outside the body that may be connected to the circulatory system or body fluid compartment in a mammal and provides for the flow of blood or fluid through the tube or conduit by natural (e.g., heart) or artificial (e.g., mechanical pump) circulation. An extracorporeal device of the present invention is configured to be disposed in an extracorporeal circuit.

The term "anchoring element" as used in this specification embraces any structure that may be inserted into the lumen of an extracorporeal circulatory system blood tube or conduit and that, once inserted, may be anchored, for example, by hooks, barbs, or stents, to an inner surface of the tube or conduit. In an exemplary embodiment, the anchoring element may be a blood clot filter-type structure. A variety of blood clot anti-migration filters useful in the practice of the invention are known in the art. The currently preferred anchoring element is an anti-migration filter known as a "Greenfield® vena cava filter". Useful Greenfield® vena cava filters are described in detail in U.S. Pat. Nos. 4,817,600 and 5,059,205, the entire disclosures of which are incorporated by reference.

The term "capsule" as used in this specification embraces any hollow structure dimensioned to fit within the lumen of a tube or conduit used in an extracorporeal circuit and does not occlude or prevent blood or fluid flow. In one embodiment, the capsule is held in place within the extracorporeal blood circuit by anchoring element(s). For example, the capsule may be retained upstream of the anchoring element, alternatively, the anchoring element may be located downstream of the anchoring element and retained in place by an attachment, for example, a hook or tether, extending from the anchoring element to the capsule. In addition, the capsule may be conical or wedge-like in shape to decrease the turbulence of blood flowing past the capsule. In a preferred embodiment, the capsule is formed from a material that can filter particles such that particles (including cells) below a certain size can pass through and particles above a certain size are prevented from passing through. The filter forms an ultrafiltrate from the blood to minimize the entry of proteins greater than 100,000 molecular weight so that immunoglobulins can be excluded from the bathing media around the cells, especially for non-autogolous cells not to activate an immunologic response.

The capsule may include either a single hollow fiber or a bundle of hollow fibers made from a semi-permeable membrane. The semi-permeable membrane filter preferably has pores of a size sufficient to permit the diffusion of a preselected molecule or cell products therethrough but yet small enough to exclude the passage of cells therethrough. The pores preferably are designed to permit the preselected molecule produced by the cells to diffuse directly into the blood stream passing the hollow fiber while preventing the cells from migrating out of the hollow fiber and into the systemic circulation.

A variety of polymers are useful in producing the biocompatible semi-permeable membrane of the present invention. They include, but are not limited to polyalginate, polyvinylchloride, polyvinylidene fluoride, polyurethane isocyanate, cellulose acetate, cellulose diacetate, cellulose triacetate, cellulose nitrate, polysulfone, polystyrene, polyurethane, polyvinyl alcohol, polyacrylonitrile, polyamide, polymethylmethacrylate, polytetrafluoroethylene, and polyethylene oxide. In addition, useful semi-permeable membranes may be produced from a combination of such polymers.

In an embodiment, the viable cells enclosed within the semi-permeable hollow fiber(s) of the capsule, preferably are eukaryotic cells, and most preferably are mammalian cells. Although the device described herein may comprise cells which naturally produce and secrete the preselected molecule or other cell products, it is contemplated that genetically engineered cells, i.e., cells transfected with, and capable of expressing a nucleic acid encoding the pre-selected molecule, may likewise be used in the practice of the invention.

In another embodiment, the preselected molecule can be a protein, and most preferably is a hormone, for example, erythropoietin or insulin. It is contemplated, however, that the device may be used to deliver into the systemic circulation any molecule that can be produced and secreted from a viable cell. Although single cell types that produce and secrete a single preselected molecule may be used in the invention, it is understood that cells belonging to a particular cell type that produce and secrete a plurality of preselected molecules likewise may be used in the practice of the present invention. Similarly, it is contemplated that a plurality of cell types, wherein cells belonging to each cell type produce and secrete different preselected molecules, may be combined in a capsule thereby to produce a device that delivers a desirable combination of preselected molecules into the circulation.

Preferred embodiments of the device include three configurations. Each preferred configuration isolates the therapeutic cells to minimize the immune response. In a first configuration a device consists of a cartridge, a cell bearing unit which may be in the form of tubes attached to the cartridge and an anchoring system. The therapeutic cells are disposed within the tubes and the cells are isolated by the size of the pores in the tube. In a second configuration the cell bearing unit is in the form of disks that are disposed in the cartridge. The therapeutic cells on the disks are protected from immunologic rejection by isolating the disks in the cartridge and providing pores in the cartridge that prevents the cells from being exposed to undesirable elements while allowing free physiologic exchange for the cells within the extracorporeal blood or fluid stream. A third configuration is a combination of the configurations described above. Other configurations are possible.

DETAILED DESCRIPTION

The present invention provides an extracorporeal device for delivering molecules into a mammal, for example, the systemic circulation of a mammal. The device of the invention is adapted for introduction in an extracorporeal blood conduit. After introduction into the extracorporeal blood conduit, the device permits the pre-selected molecule or cell products to diffuse out of the device and into the blood stream or body cavity of the recipient, which in certain aspects does so in response to blood parameters, for example, oxygen tension in the case of erythropoietin-producing cells. Also, the glucose concentrations in the bathing media around the insulin producing cells can stimulate the production of insulin.

The embodiments of the invention have at least some of the following advantages. Because the device is extracorporeal, there is less size constraint and the cell bearing units can be sized larger than if a device was implanted. Further, because the device is not implanted in the body, the anchoring system does not need to be designed to be atraumatic. A cartridge embodiment that fits along a conduit is contemplated without an anchoring system. Because the device is not intended to be inserted in a blood vessel, the introduction of the device to the blood stream is much simpler.

The device includes a capsule that holds cell-bearing material. The cells on the cell bearing material are prevented from provoking an immunological response by isolating the cells using a porous material that creates a barrier between the blood and the cells. The barrier allows the cells to have sufficient physiological exchange (e.g., drawing sustaining nutrients and oxygen) with the blood and delivery of the metabolic products produced by the cells. The metabolic products may be in response to small messenger molecules that might be circulated in the blood stream as a result of the patient's pathologic condition. Also, the metabolic production can be stimulated by introducing a messenger molecule into the bloodstream of the patient.

An embodiment of the device of the present invention includes an anchor system that secures the device to an inner wall of a extracorporeal blood circuit. The anchor system may have arms that are adapted to be in a reduced profile configuration during delivery into the blood circuit and expand into a delivered profile so that the amrS expand and extend to the blood conduit. The anchoring system may use hooks, barbs, or stents disposed upon the arm of the anchor system. The anchoring system is designed such that when anchored to the wall of the blood conduit, the system permits blood in the vessel to pass through and around the device.

The device includes a shape, e.g., cone, facing upstream that minimizes turbulence of blood as it flows beyond the capsule. In one embodiment the device comprises a semipermeable housing containing viable cells which produce and secrete the pre-selected molecule. The viable cells may be disposed on a flat surface such as a disk. In another embodiment the cells are contained within porous tubes that allow the physiologic activity of the cells to occur and from which the preselected molecule or cell products can flow into the bloodstream or body fluids. The tubes may extend beyond the capsule.

Figure 1:
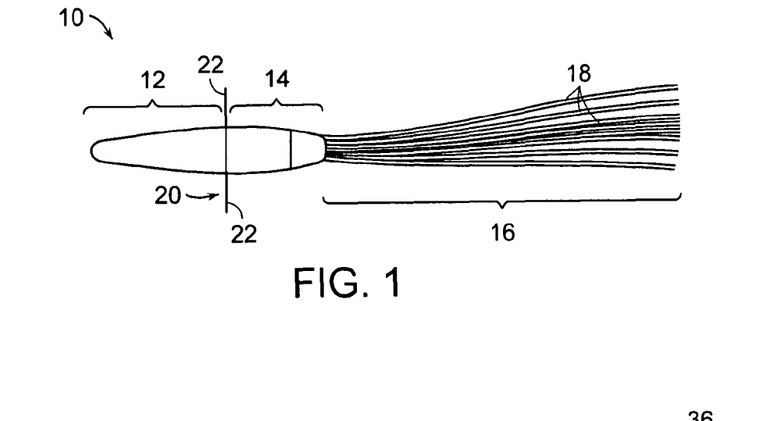
FIG. 1 is a perspective side view of a device according to an embodiment of the present invention.

Embodiments of the present invention will now be described in greater detail with reference to the attached drawings, which are provided for purposes of illustration and are not meant to be limiting of the scope of the invention. Referring to the drawings, FIG. 1 illustrates schematically a device 10 useful in the practice of an embodiment of the present invention. In FIG. 1, the device 10 includes a nose cone 12 and a body 14 that is used to secure a cell bearing unit 16 comprised of hollow fibers 18 made of a semi-permeable material which encloses viable cells for delivering the preselected molecules. In this embodiment, the nose cone and the body of the device support the cell bearing unit 16 comprising the hollow fibers 18.

The viable cells may be attached to an inner surface of a fiber. Whether the cells are attached to the inner surface will depend upon the cell type included in the device. For example, some cell types grow in an anchorage dependent manner upon a solid surface while other cell types have no anchorage dependency and grow in suspension. The choice of cell type, however, is dependent upon the desired application.

The device of FIG. 1 is attached to an extracorporeal blood circuit by a suitable anchor system 20 that includes anchors 22. Two anchors 22 are illustrated, however, more or fewer than two could be used in a suitable design. The anchors are configured to hold the device securely in the extracorporeal conduit (shown in FIG. 8). The anchors may be retractable in a reduced profile for delivery and expanded into a deployed profile when the device is at the appropriate location on the conduit. Various springy or resilient biocompatible material may be used including nitinol or other spring material.

Figure 2:
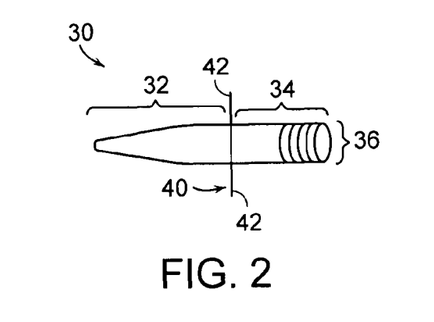
FIG. 2 is a perspective side view of a device according to another embodiment of the present invention.
Figure 3:
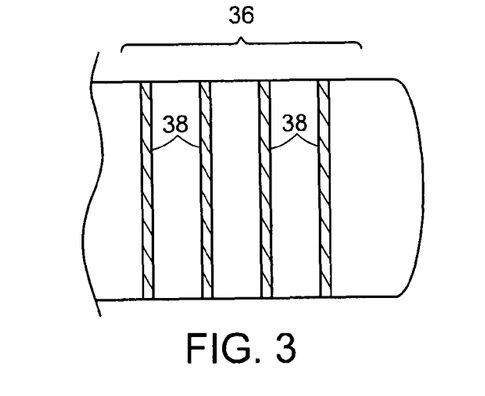
FIG. 3 is a detail cross section of the downstream end of the device illustrated in FIG. 2.
Figure 4:
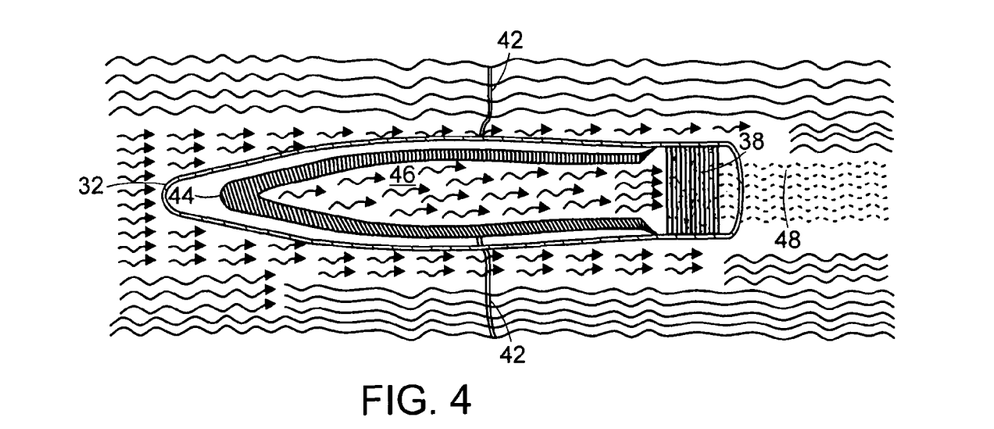
FIG. 4 is a cross section of the device illustrated in FIG. 2 and shows the flow of fluid through the device.

FIGS. 2-4 illustrate another embodiment of the invention where the device 30 includes a nose cone 32 and a body 34 into which the cell bearing unit 36 is attached. In this embodiment, the cell bearing unit includes several semi-permeable membrane disks 38 which contain the viable cells. The size and number of disks used may vary depending on the type and amount of the preselected molecule being delivered. It is contemplated that semi-permeable membranes may be defined by either the same or different polymeric compositions. An anchoring system 40 with anchors 42 is structured similarly and operates in a similar manner as the anchoring system described in connection with FIG. 1.

A detail view of the disk 38 is illustrated in FIG. 3. The disk 38 is approx 1 cm in diameter and has, in one embodiment, cells associated with the membranes such that the cells are exposed to the blood or fluid constituents for nutrients and the cells are able to deliver the desired product(s) for the blood. In a preferred embodiment the membranes have a trabecular structure to enhance the exchange of physiologic material. In an embodiment, the disk is similar to a coin that is trabeculated and porous. The configuration allows flow through of various media components and anchorage dependent growth especially of epithelial cells at higher tissue density.

FIG. 4 illustrates a device in a blood conduit. Blood flow is illustrated by the wavy lines. A filter 44 is provided in the device to exclude large blood constituents, e.g., macrophages and immunoglobulins, from causing an undesired immune response with the cells on the disks 38. The filtered material 46, also called ultrafiltrate, is allowed to flow across the disks 38. In other embodiments they may flow through the membranes. The ultrafiltrate provides sustaining nutrients to the cells on the disk and carries away the products of cell metabolism. The resultant stream of ultrafiltrate blood and the products of metabolism is schematically illustrated as wavy dotted lines 48. Optionally, a filter can be used at the downstream outlet of the device.

Figure 5:
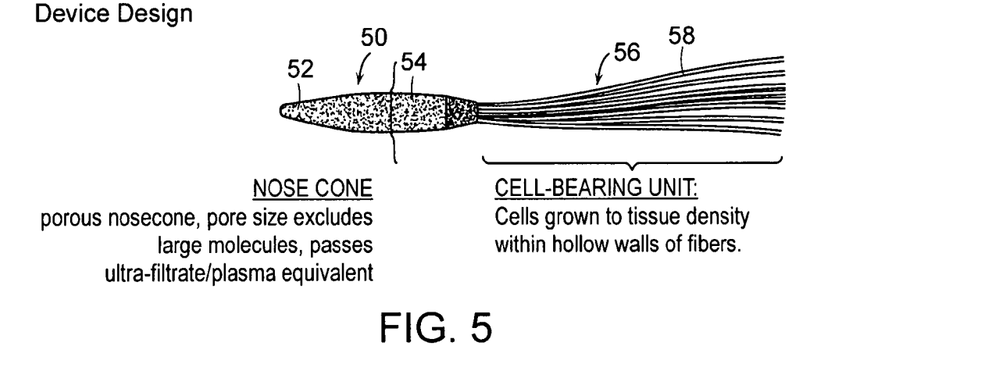
FIG. 5 is a perspective view of another embodiment of the invention.
Figure 6:
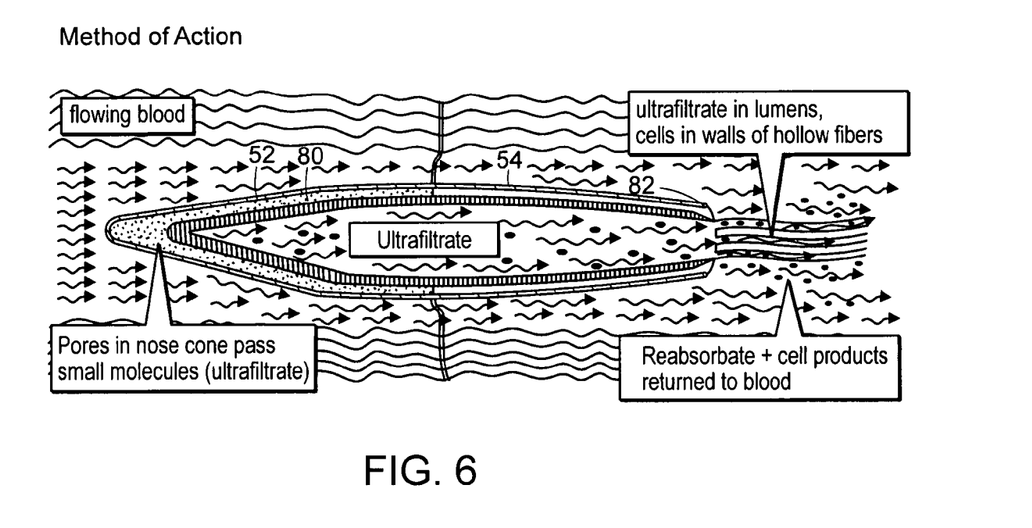
FIG. 6 is a schematic cross section illustrating the embodiment of FIG. 5.
Figure 7:
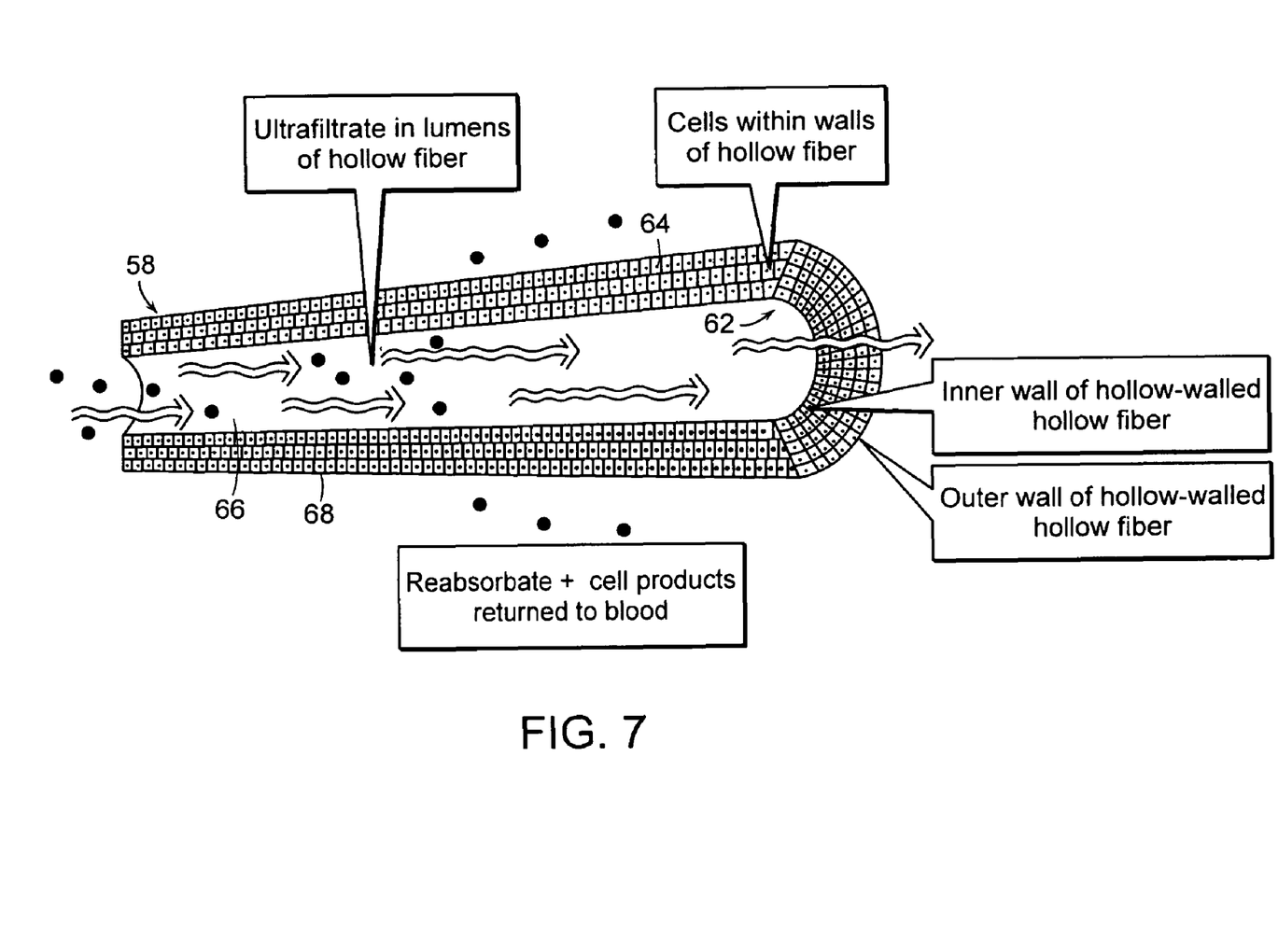
FIG. 7 is a detail view of an ultrafiltrate tube illustrated in FIGS. 5 and 6.

In another embodiment of the invention, illustrated in FIGS. 5-7, the hollow tubes may be constructed to provide a multi-layered structure. The device 50 includes a porous nose cone 52 that filters out large blood constituents and a body 54 that holds one end of a series of hollow tubes 56. A single hollow tube is identified by reference numeral 58.

The body includes a manifold (illustrated in FIG. 6) that distributes the filtered blood into the center of the hollow tubes, one cross section of which is illustrated in FIG. 7. The distal end of the hollow tubes may be blocked (not illustrated) to provide desireable flow dynamics or to prevent the flow of unfiltered blood from being introduced to the tubes. As such, the flow path of the filtered blood can be through the tube or through the wall, depending on the desired construct. In either case, sufficient sustaining nutrients should be available to the cells within the wall of the tube.

As illustrated in FIG. 7, the hollow tube 58 includes a central lumen 62 through which the filtered blood passes. Cells 64 are disposed along a tubular medium (illustrated in axial cross section) between an inner wall 66 and an outer wall 68 and cells are disposed such that filtered blood or fluid travels across the cells. The cells are thus provided with life sustaining nutrients enabling the production of desirable cell products. In the embodiment illustrated, the outer wall of the hollow tube 58 allows the cellular products to be delivered through the tube but does not allow large particles into the tube to contact the cells. Both the inner and outer wall may have such filtering function.

Alternatively, the end of the tube is not blocked and the filtrate is allowed to bath the cells and has a sufficient flow rate such that the cells are provided with the proper amount of nutrients and the unfiltered blood is not allowed to travel upstream to the cells.

The Anchoring System

As mentioned above, anchoring systems that may be used in the instant invention include devices that provide blood clot filtering or blood vessel stents. Useful anchoring elements are characterized by their ability to be anchored within the lumen of a conduit without occluding or preventing blood flow. One of the advantages of the present invention is that the extracorporeal device anchoring system does not have to be designed to be secured in a blood vessel without damaging the blood vessel. This minimizes the concern for tissue damage.

Blood clot filters are used routinely by medical practitioners to prevent the migration of potentially life threatening blood clots within the vasculature. Blood clot filters typically are designed to be implanted and anchored within the lumen of a blood vessel. When implanted, the anti-migration filters permit blood in the vessel to pass while simultaneously trapping blood clots. The devices and techniques useful toward attaching a filter to a blood vessel can be applied to extracorporeal devices. Of course, because the device is not intended to be introduced into the vasculature, the design of the anchors need not have the high level of precision required for their use.

Filters described in U.S. Pat. Nos. 4,817,600 and 5,059,205, referred to in the art as Greenfield® filters and available from Medi-Tech®, Boston Scientific Corporation, Natick, Mass., are particularly well suited to the practice of the invention. The cone-shaped Greenfield® vena cava filters are designed to provide maximal entrapment area for trapping blood clots while maintaining patency of the blood vessel after trapping emboli. The spacing between the six legs of the Greenfield® vena cava filters ensures the trapping of emboli greater than 3 mm (Greenfield et al. (1989) "Venous Interruption" Chapter 68, pp. 929-939 in "Haimovici's Vascular Surgery Principles and Techniques, Third Edition," Appleton and Lange, Norwalk, Conn./San Mateos, Calif.). Accordingly, the filters may be able to capture capsules greater than 3 mm in diameter. In another embodiment of the invention the device is incorporated into a tube that is inserted into an extracorporeal conduit. In this embodiment the anchors are unnecessary because the device is secured within the tube.

Device Design

The extracorporeal drug delivery device of the various embodiments of the present invention may be capable of delivering a preselected drug or cell products over an extended period of time. Because the device is not designed to be implanted, the size of the capsule can be scaled for higher delivery rates by increasing the size of the capsule and the drug delivery media.

Because the device permits delivery of the preselected molecule over defined periods of time, another important consideration in the design of the device is the configuration that will maintain the viability of the cells enclosed in the device. It is understood that a variety of factors, for example: the supply of oxygen and nutrients to the cells in the capsule; the removal of waste products from the cells in the capsule; the minimization of host immune responses directed against the cells in the capsule; the proliferative activity of the cells; and whether cells located at the center of the capsules are susceptible to pressure necrosis, all of which may influence the design and preparation of a cell containing tube(s).

In addition to adequate aeration, it is important that the encapsulated cells obtain sufficient amounts of essential nutrients from the blood supply to remain viable. The transport oxygen is almost entirely by diffusion and this is a significant aspect in maintaining cell viability. Once the geometry of a hollow fiber has been optimized for oxygen transport, then the hollow fiber inherently will be able to permit the diffusion of adequate amounts of nutrients into the lumen of the capsule from the blood stream. Similarly, such a geometry is contemplated also to permit diffusion of cell metabolites, including, waste products and the preselected molecule, out of the hollow fiber and into the blood stream.

The hollow fibers preferably are produced from a semi-permeable membrane having pores dimensioned to permit the diffusion of oxygen and nutrients into the lumen of the hollow fiber while permitting the efflux of cellular waste products and the pre-selected molecule out of the hollow fiber. In addition, the pores preferably are dimensioned to exclude the passage of cells therethrough. Accordingly, the pores are designed to prevent migration of the viable cells from the lumen of the hollow fiber into the blood steam, thereby maintaining the implanted cells at a single location in the host to facilitate their subsequent removal if or when necessary. The pores also are designed to prevent the influx of the hosts immune cells, for example, macrophages and lymphocytes, which if allowed to enter the lumen of the hollow fibers may be detrimental to the viability of the cells enclosed therein. The membrane, therefore, provides an immuno-priviledged environment that protects cells enclosed therein from an immune response. This may be an important consideration if the implanted cells are non-autologous in nature. If autologous cells are used per size restrictions longer than molecular dimension then the design would be modified accordingly.

The hollow fibers comprising, or for incorporation within, the capsule may be produced from biocompatible polymers which include, but are not limited to, polyvinylchloride, polyvinylidene fluoride, polyurethane isocyanate, polyalginate, cellulose acetate, cellulose diacetate, cellulose triacetate, cellulose nitrate, polysulfone, polystyrene, polyurethane, polyvinyl alcohol, polyacrylonitrile, polyamide, polymethylmethacrylate, polyethylene oxide, polytetrafluoroethylene or copolymers thereof. A summary of currently available hollow fibers, including methods of manufacture and the names of commercial suppliers, is set forth in Radovich (1995) "Dialysis Membranes: Structure and Predictions" Contrib Nephrol., Basel, Karger, 113:11-24, the entire disclosure of which is incorporated herein by reference. In addition, polytetrafluorethylene polymer hollow fibers are available commercially from Impra, Inc., Tempe, Ariz. or W. L. Gore and Associates, Flagstaff, Ariz. U.S. Pat. No. 6,716,208, the contents of which is incorporated by reference, provide more details of the components of the device.

Disks

The disks provide a suitable material onto which the cells can be disposed. In a preferred form. The disks have a trabecular structure that allows the cells to grow into the medium. Alternatively, the cells may be disposed on the surface of the membrane. The disk material may consist of a variety of different types of compounds, including ceramics, carbon, and metallic substances. In one embodiment, the disks are made from carbon material coated with niobium.

Use of the Device

Cell therapy presents itself as a new approach to the treatment of acute and chronic diseases. This therapeutic approach has its origins in the growing appreciation that most disease processes are not due to the lack of a single protein but develop due to alterations in complex interactions of a variety of cell products. Cell therapy depends on cell and tissue culture methodologies to expand specific cells to replace important differentiated processes deranged or lost in various disease states. Recent approaches have made progress by placing cells into hollow fiber bioreactors or encapsulating membranes as a means to deliver cell activities to a patient, requiring complex extracorporeal pump systems and large bioreactor devices. One clinical disorder that may be treatable with cell therapy is the systemic inflammatory response syndrome, or SIRS. It is a catastrophic sequela of a variety of clinical insults, including infection, pancreatitis, and cardiopulmonary bypass, and claims over forty thousand lives in the U.S. each year. The most common cause of SIRS is bacteria-induced septic shock. The exceptionally high mortality associated with the syndrome is due in part to the development of the highly lethal multiple system organ failure syndrome (MOF) in a subset of patients with SIRS.[references 1,2]

One area that presents opportunities is the development of miniaturized cell therapy devices containing renal tubule cells, which play an important immunologic regulatory role in septic shock. The successful development of a prototype is an important step toward allowing cell therapy to be delivered in a simple extracorporeal cassette without extracorporeal pump systems, thereby expanding this therapy to a broader indication, especially early severe sepsis syndrome prior to established acute renal failure (ARF).

An extracorporeal device utilizing a standard hemofiltration cartridge containing approximately $10^8$ renal tubule cells grown from adult stem/progenitor cells as confluent monolayers along the inner surface of the fibers has been successfully fabricated with human cells.[reference 4] This initial cell therapy device is large (12×4-in cylinder) and requires an additional extracorporeal pump circuit to deliver blood and plasma ultrafiltrate to the cell-containing device. These elements were designed as an add-on to current dialysis treatment in patients with ARF.

The successful creation of the miniature device proposed has the potential to lead to a variety of other cell therapy devices including "wearable artificial organs". Current cell therapy approaches target the use of stem cells for neurodegenerative disorders (Parkinson's, Alzheimer's), spinal cord injury, heart disease (congestive heart failure, myocardial infarct), pancreas disease (diabetes), liver disease (cirrhosis, hepatitis), kidney disease (end-stage renal disease [ESRD], ARF), blood (sickle cell anemia), muscle disorders (muscular dystrophy), skin (burns), and bones (arthritis, osteoporosis). From a market standpoint, the value of cell-based markets is estimated to be $26.5 billion in 2005, $56.0 billion in 2010, and $96.0 billion in 2015. More than 300 companies are involved in cell therapy. The near-term market for the use of renal cell devices is also very large and includes (U.S. only): ARF (100,000 patients, $2 billion market), ESRD (400,000 patients, $20 billion cost), and cardiorenal syndrome (350,000 patients, $25 billion cost).

Figure 8:
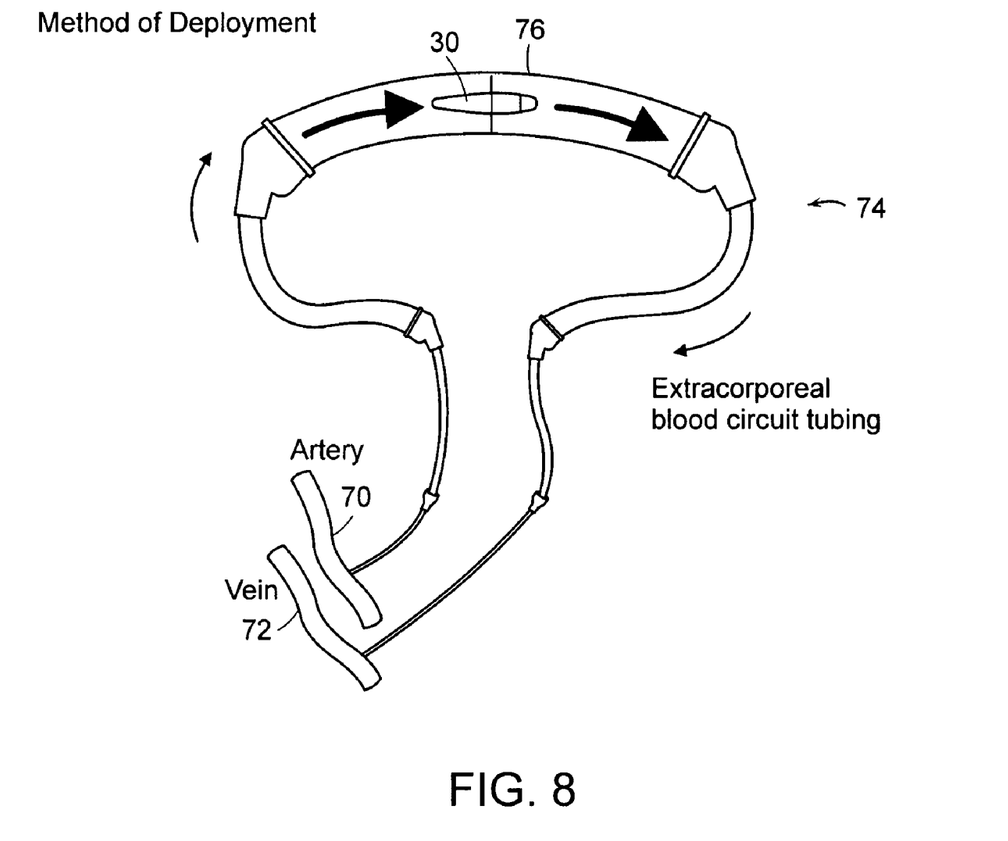
FIG. 8 is a schematic view of an extracorporeal blood circuit that can be used with embodiments of the present invention; and, FIGS. 9-12 are graphs representing testing of embodiments of the present invention.

Early prototype formulation of miniaturized cell therapy devices are schematized in FIGS. 1 and 8. Of note, this arteriovenous catheter circuit does not require blood pumps for blood flow through the circuit.

Fabrication and in vitro testing of first prototype. The first prototype to be evaluated is depicted as in FIG. 1. This prototype will be fabricated to contain $1.0 \times 10^8$ renal tubule cells in high density growth within the hollow fibers. Preliminary data suggest that 30 hollow fibers (250 μm×10 cm in length) can maintain $1.0 \times 10^8$ cells in a high-flow situation with adequate oxygenation and nutrient supply in vitro. Initial studies with permanent cell lines have demonstrated that a simpler hollow fiber prototype can maintain this degree of cell density over several weeks. If these initial prototypes are able to maintain cell viability in a cell incubator over 3-5 days, they will be available for efficacy testing in the porcine septic shock model. This experiment is an important proof of concept that renal tubule cells can be placed and maintained in a hollow fiber device with high cell density to provide enough cells in a miniaturized cassette.

Fabrication and in vitro testing of a second prototype with cryopreservation storage capacity. Prototype development of a second cell therapy device is also schematized in FIG. 1. This second device, illustrated in FIGS. 2 and 3, contains a series of discs forming a trabecular structure on which cells attach and grow. Preliminary data suggest up to $1.0 \times 10^7$ cells can grow on each disc, which is made of a new biomaterial carbon coated with niobium. Ten discs can be placed within a cartridge that acts as a semipermeable membrane to produce plasma ultrafiltrate. This high rate of ultrafiltrate flow provides nutrients and oxygen to the cells on the discs to maintain viability, functionality, and efficacy, while preventing immunologic rejection. Preliminary data have also suggested that the cells on the disc can be cryopreserved and maintain adherence and viability upon thawing and warming to body temperature. Thus, distribution of cell therapy devices will be made simpler with onsite freezer storage, rather than storage in a 37° C. incubator and rapid transport to the clinical care setting from the manufacturing site. When in vitro experiments with this prototype demonstrate maintenance of cell viability over 3-5 days, in vivo testing in the porcine model can proceed.

The extracorporeal device of various embodiments of the present invention can be used with a blood or fluid conduit as illustrated in FIG. 8. The blood from a patient can be through an Aterio Venous (AV) line that could be used in dialysis. Also, venous to veneous (VV) lines can be used. As illustrated an artery 70 and vein 72 can be used to extract blood and reintroduce blood for an extracorporeal circuit 74. Various suitable connections may be used to increase the diameter of the conduit. The device 30 is illustrated as being attached to the largest conduit 76. The lines may circulate body fluids, for example, peritoneal fluid that is removed from the peritoneum and circulated outside the body where the device is able deliver the desired molecule to the fluid and then reintroduced into the peritoneum.

It is understood, however, that the physicians judgment based upon clinical circumstances should determine on a case by case basis the optimal mode for introducing the device as well as the optimal location for anchoring the device. Such judgments are contemplated to be within the scope of expertise of the skilled physician.

Practice of the invention will be still more fully understood from the following examples, which are presented herein for illustration only and should not be construed as limiting the invention in any way.

Two different device designs are envisioned for the therapeutic delivery system:
1. Cells would be grown on Nb-coated carbon based, disc-shaped scaffolds (refer to page 3 for disc system specifications). These cell-seeded discs would be grown in culture and then cryoperserved. Discs could be shipped frozen to clinical sites were they could be kept frozen until required for cell-based therapy. Thawed discs could be placed in the device housing just prior to therapy. The number of discs used per therapy session (loaded into the holding device) could be varied depending on the cellular dose required.
2. Cells resuspended in a biomatrix 3-D gel would be seeded into the lumen of a hollow fiber bioreactor. 2 methods of deployment to the clinical site are to be tested: 1) mature cultured cell loaded bioreactors would be shipped as needed under optimal shipping conditions (to be determined) and then used in the clinical setting. 2) A tube of cryoperserved cells and a tube of pre-mixed liquid biomatrix would be sent to the clinical site. These could be stored until needed. Upon clinical need, cells would be thawed, mixed with biomatrix and syringe loaded into the bioreactor. The cryoperserved tube could contain various cell numbers for dose dependent therapy.

Figure 9:
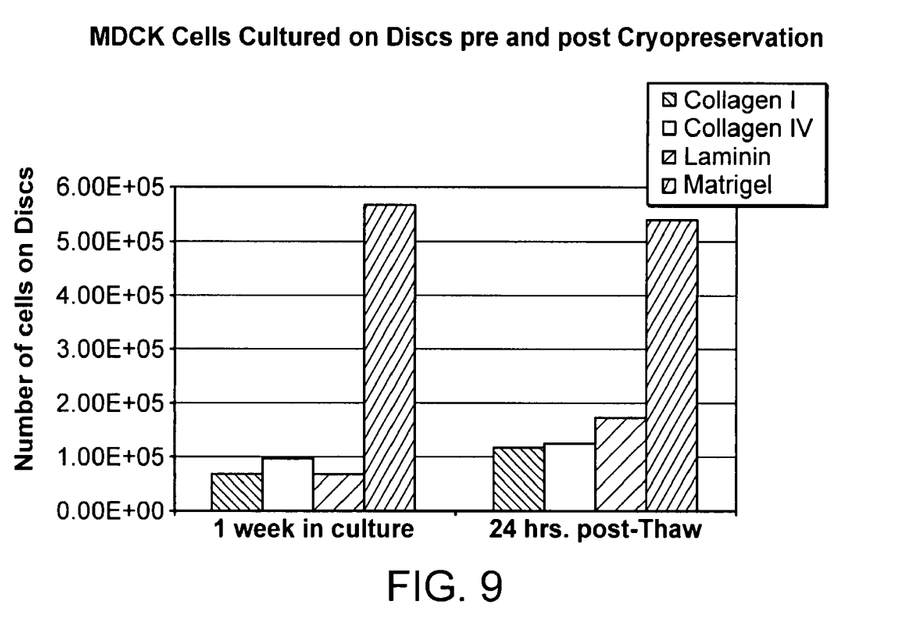

Cell Seeded Nb-Coated Carbon Based, Disc-Shaped Scaffolds:

An immortalized renal cell line (MDCK) was seeded unto Nb-coated carbon based discs. Prior to cell seeding, discs were coated with either collagen I, collagen IV, laminin, or matrigel. Seeding densities were $10^6$ cells/disc. The discs were maintained in a spinner culture for 1 week. Cell seeded discs were then cryoperserved, stored in liquid nitrogen and then thawed, with a non-stir rest period under tissue culture conditions of 2-4 hours post thaw. Discs were then reinstated in spinner culture bottles and assayed for cell density 24 hours post thaw. Lactate production was utilized to determine cell expansion on the discs. MDCK cell densities on discs with various bio-matrix coatings pre and post cryoperservation are depicted in the graph of FIG. 9.

Figure 10:
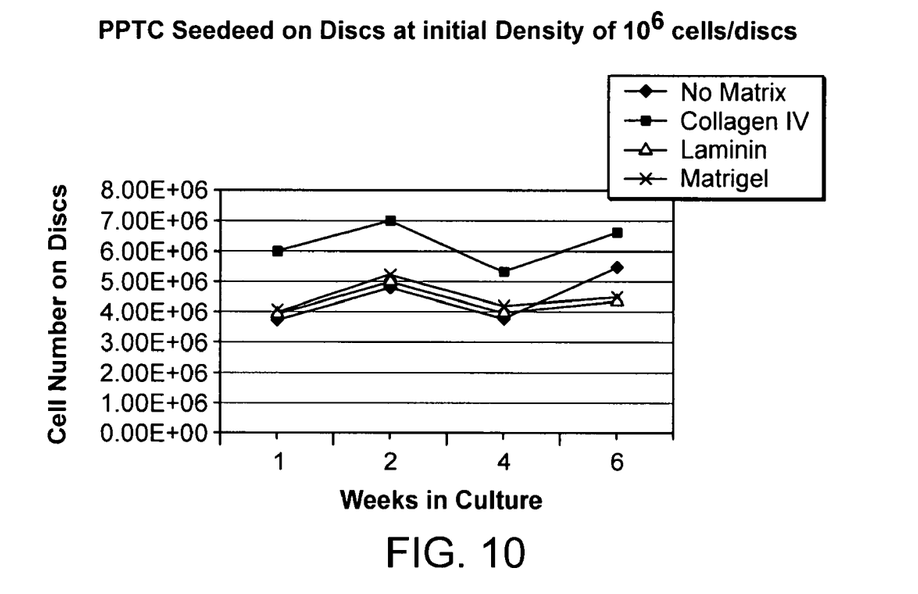
Figure 11:
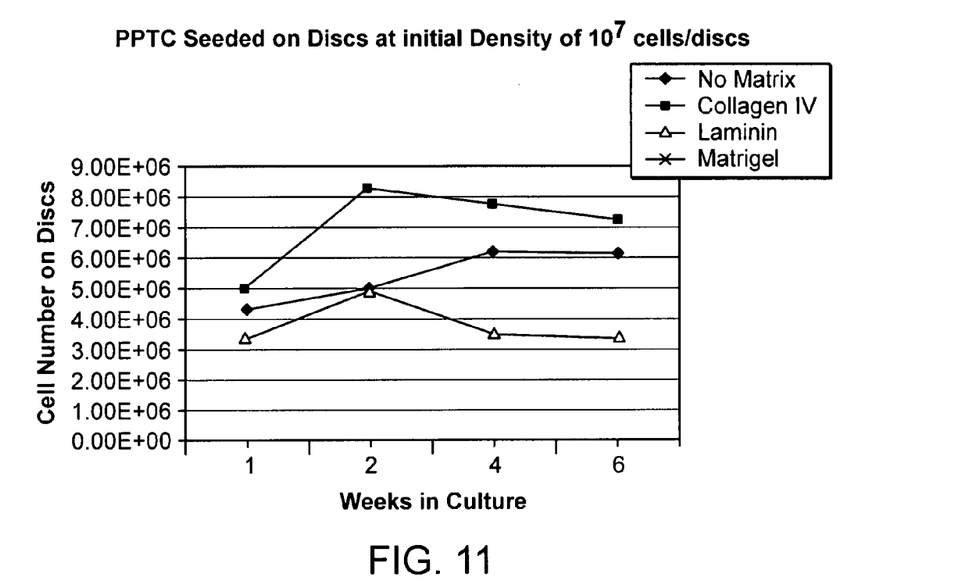

In order to ascertain if primary cells could also be maintained on the Nb-coated carbon based discs, primary porcine renal proximal tubule cells (PPTC) were seeded on discs coated with various bio-matrixes (either no matrix, collagen IV, laminin, or matrigel) at $10^6$ and $10^7$ cells/disc. Cell seeded discs are currently being maintained in spinner culture. Primary porcine renal tubule cell growth rates on discs, as determined by lactate production, are depicted FIGS. 10 and 11.

Figure 12:
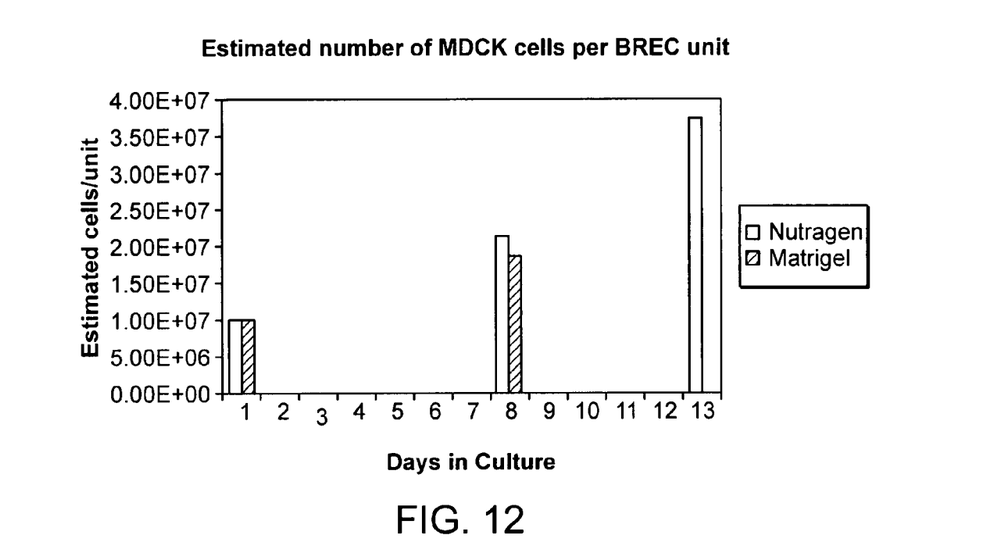

Hollow Fiber Bioreactor Containing Cells Resuspended in a Biomatrix 3-D Gel:

Cells from an immortalized renal cell line (MDCK) resuspended in either 1) nutragen (collagen I (3.12 mg/mL) gel supplemented with laminin (100 ug/mL) and collagen IV (100 ug/mL)) or 2) matrigel were seeded into hollow fiber bioreactors at a density of $2.06 \times 10^7$ cells/mL of gel. Cell loaded bioreactors were maintained in culture for 8 (matrigel) and 13 (nutragen) days, with cell density assessed via lactate production. Results are depicted in the FIG. 12. BREC refers to Bioartificial Renal Epithelial Cell.

Other Embodiments and Clinical Objectives

The invention may be embodied in other specific forms without departing from the spirit or essential characteristics thereof. The present embodiments are therefore to be considered in all respects as illustrative and not restrictive.

Appendix I. Literature Cited
1. Pinsky M R, Vincent J L, Deviere J, Alegre M, Kahn R J, Dupont E: Serum cytokine levels in human septic shock. *Chest* 1993; 103:565-576.
2. Marty C, Misset B, Tamion F, Fitting C, Carlet J, and Cavallion J M: Circulating interleukin-8 concentrations in patients with multiple organ failure of septic and nonseptic origin. *Crit Care Med* 1994; 22:673-679.
3. Humes H D, Buffington D A, Lou L, Abrishami S, Wang M, Xia J, and Fissell W H: Cell therapy with a tissue-engineered reduces the multiple-organ consequences of septic shock. *Crit Care Med* 2003; 31:2421-2428.
4. Humes H D, Fissell W H, Weitzel W F, et al: Metabolic replacement of renal function in uremic animals with a bioartificial kidney containing human cells. *Am J Kidney Dis* 2002; 39(5):1078-1087.
5. Humes H D, Buffington D A, MacKay S M, et al: Replacement of renal function in uremic animals with a tissue-engineered kidney. *Nat Biotechnol* 1999; 17:451-455.
6. Humes H D, MacKay S M, Funke A J, et al: Tissue engineering of a bioartificial renal tubule assist device: In vitro transport and metabolic characteristics. *Kidney Int* 1999; 55:2502-2514.

7. Fissell W H, Dyke D B, Weitzel W F, et al: Bioartificial kidney alters cytokine response and hemodynamics in endotoxin challenged dogs. *Blood Purif* 2002; 20:55-60.
8. Fissell W H, Lou L, Abrishami S, et al: Bioartificial kidney ameliorates gram-negative bacteria-induced septic shock in uremic animals. *J Am Soc Nephrol* 2003; 14:454-461.
9. Humes H D, Buffington D A, Lou L, et al: Cell therapy with a tissue-engineered kidney protects against the multi-organ consequences of septic shock. *Crit Care Med* 2003; 31:2421-2428.
10. Humes H D, Weitzel W F, Bartlett R H, Swaniker F C, Paganini E P, Luderer J R, and Sobota J: Initial clinical results of the bioartificial kidney containing human cells in ICU patients with acute renal failure. *Kidney Int* 2004; 66:1578-1588.
11. Tumlin J, Wali R, Brennan H D, and Humes H D: Effect of the renal assist device (RAD) on mortality of dialysis-dependent acute renal failure: A randomized, open-labeled, multicenter, Phase II trial [Abstract]. *J Am Soc Nephrol* 2005; 16:46 A.
12. Williams W, Tumlin J, Murray P, Tolwani A, RAD-002 Study Investigators: Renal bioreplacement therapy (RBT) reduces mortality in ICU patients with acute renal failure (ARF). *J Am Soc Nephrol* 2006; 17:49 A.

The invention claimed is:

1. An extracorporeal cell based therapeutic device comprising: (a) a housing defining an interior space and having viable renal cells disposed therein; and (b) a frozen, niobium-coated carbon scaffold having a trabecular structure disposed within the housing, wherein the viable renal cells are attached to the scaffold.

2. The device of claim 1, wherein the scaffold comprises at least one disk and the cells are disposed on the at least one disk.

3. The device of claim 1, wherein the scaffold is porous.

4. The device of claim 1, wherein the scaffold comprises a bio-matrix coating selected from collagen IV, collagen I, laminin, and matrigel.

5. The device of claim 1, wherein the device further comprises an anchor system which is capable of attaching the device to an extracorporeal tube.

6. The device of claim 1, wherein the housing defines a plurality of pores.

7. The device of claim 1, wherein the device further comprises a porous barrier between the viable cells and a body fluid present when in use.

8. The device of claim 7, wherein the porous barrier produces ultrafiltrate.

9. The device of claim 1, wherein the device is adapted for use with peritoneal fluid.

10. A cryopreserved composition comprising renal cells attached to a frozen scaffold comprising a carbon material coated with niobium and comprising a trabecular structure.

11. The scaffold of claim 10, wherein the scaffold comprises a bio-matrix coating selected from collagen IV, collagen I, laminin, and matrigel.

12. The scaffold of claim 10, wherein the substrate is porous.

* * * * *

UNITED STATES PATENT AND TRADEMARK OFFICE
CERTIFICATE OF CORRECTION

| | |
|---|---|
| PATENT NO. | : 8,048,419 B2 |
| APPLICATION NO. | : 11/670123 |
| DATED | : November 1, 2011 |
| INVENTOR(S) | : H. David Humes |

It is certified that error appears in the above-identified patent and that said Letters Patent is hereby corrected as shown below:

In Claim 11, column 14, line 24, replace "scaffold" with --composition--.

In Claim 12, column 14, line 27, replace "scaffold" with --composition-- and "substrate" with --scaffold--.

Signed and Sealed this
Twenty-fourth Day of April, 2012

David J. Kappos
*Director of the United States Patent and Trademark Office*